(12) United States Patent
Fless et al.

(10) Patent No.: US 6,372,886 B1
(45) Date of Patent: Apr. 16, 2002

(54) **EXPRESSION AND PURIFICATION OF KRINGLE DOMAINS OF HUMAN APOLIPOPROTEIN (A) IN *E. COLI***

(75) Inventors: Gunter M. Fless, Hinsdale; Angelo M. Scanu, Chicago, both of IL (US)

(73) Assignee: Arch Development Corp., Chicago, IL (US)

( * ) Notice: Subject to any disclaimer, the term of this patent is extended or adjusted under 35 U.S.C. 154(b) by 0 days.

(21) Appl. No.: 08/240,839

(22) Filed: May 11, 1994

Related U.S. Application Data

(62) Division of application No. 07/902,646, filed on Jun. 23, 1992, now abandoned.

(51) Int. Cl.$^7$ ........................... C07K 1/00; C07K 16/00; C07K 14/00; A61K 38/00
(52) U.S. Cl. ...................... 530/350; 435/69.1; 530/300; 530/324; 530/395
(58) Field of Search .................. 435/69.1; 530/300, 530/324, 395, 350

(56) References Cited

PUBLICATIONS

Mauna, C.V. et al. *Gene* 74:365–373 (1988).*
Wei, C.–F. et al. *PNAS* 82:7265–7269 (1985).*
Castellino et al., "The Existence of Independent Domain Structures in Human Lys$_{77}$–Plasminogen*," *The Journal of Biological Chemistry*, 256 (10) :4778–4782, 1981.
Cleary, et al., "Purification and Characterization of Tissue Plasminogen Activator Kringle–2 Domain Expressed in *Escherichia coli*," *Biochemistry*, 28:1884–1891, 1989.
Copeland et al., "The Structure of Human Acidic Fibroblast Growth Factor and Its Interaction with Heparin," *Archives of Biochemistry and Biophysics*, 289 (1) :53–61, 1991.
Eaton et al., "Partial amino acid sequence of apolipoprotein(a) shows that it is homologous to plasminogen," *Proc. natl. Acad. Sci. USA*, 84:3224–3228, 1987.
Fless et al., "Heterogeneity of Human Plasma Lipoprotein (a)," *The Journal of Biological Chemistry*, 259(18) :11470–11478, 1984.
Fless et al., "Isolation of apolipoprotein(a) from lipoprotein(a)," *Journal of Lipid Research*, 26:1224–1229, 1985.
Fless et al., "Physicochemical Properties of Apolipoprotein(a) and Lipoprotein(a–) Derived from the Dissociation of Human Plasma Lipoprotein (a)*," *The Journal of Biological Chemistry*, 261(19) :8712–8718, 1986.
Gaubatz et al., "Human Plasma Lipoprotein [a]," *The Journal of Biological Chemistry*, 258(7) :4582–4589, 1983.
Gaubatz et al., "Polymorphic forms of human apolipoprotein [a]: inheritance and relationship of their molecular weights to plasma levels of lipoprotein[a]," *Journal of Lipid Research*, 31:603–613, 1990.

Lackner et al., "Molecular Basis of Apolipoprotein (a) Isoform Size Heterogeneity as Revealed by Pulsed–Field Gel Electrophoresis," *J. Clin. Invest.*, 87:2153–2161, 1991.
Matsuka et al., "Fluorescence spectroscopic analysis of ligand binding to kringle 1+2+3 and kringle 1 fragments from human plasminogen," *Eur. J. Biochem.*, 190:93–97, 1990.
McLean et al., "cDNA sequence of human apolipoprotein(a) is homologous to plasminogen," *Nature*, 330:132–137, 1987.
Menhart et al., "Construction, Expression, and Purification of Recombinant Kringle 1 of Human Plasminogen and Analysis of Its Interaction with ω–Amino Acids," *Biochemistry*, 30:1948–1957, 1991.
Morrisett et al., "Structural Properties of Apo(a) : A Major Apoprotein of Human Lipoprotein(a)," In: *Lipoprotein(a)* Scanu, A.M. (Ed.); Academic Press, New York :53–74, 1990.
Mulichak et al., "Crystal and Molecular Structure of Human Plasminogen Kringle 4 Refined at 1.9–Å Resolution," *Biochemistry*, 30:10576–10588, 1991.
Scanu and Fless, "Lipoprotein (a) Heterogeneity and Biological Relevance," *J. Clin. Invest.*, 85:1709–1715, 1990.
Trexler and Patthy, "Folding autonomy of the kringle 4 fragment of human plasminogen," *Proc. Natl. Acad. Sci. USA*, 80:2457–2461, 1983.
Trieu et al., "Interaction of Apolipoprotein(a) with Apolipoprotein B– containing Lipoproteins," *The Journal of Biological Chemistry*, 266(9) :5480–5495, 1991.
Wilhelm et al., "Functional Properties of the Recombinant Kringle–2 Domain of Tissue Plasminogen Activator Produced in *Escherichia coli*," *The Journal of Biological Chemistry*, 265(24) :14606–14611, 1990.
Wu et al., "The Refined Structure of the ε–Aminocaproic Acid Complex of Human Plasminogen Kringle 4," *Biochemistry*, 30:10589–10594, 1991.
Sangrar et al., "Expression and characterization of apolipoprotein(a) kringle IV types 1, 2 and 10 in mammalian cells," *Protein Engineering*, 7(5) :723–731, 1994.

* cited by examiner

*Primary Examiner*—Ponnathapu Achutamurthy
*Assistant Examiner*—Manjunath N. Rao
(74) *Attorney, Agent, or Firm*—Fulbright & Jaworski

(57) ABSTRACT

Methods for the expression of kringle domains of apoliprotein(a) are described. The domains, including kringle 4 domains and the unique kringle 5 domain, are efficiently expressed as fusion proteins from transformed *Escherichia coli* host cells. The fusion polypeptides may be employed directly to generate antibodies to human lipoprotein (a) or cleaved to provide the pure kringle polypeptide. Monoclonal antibodies to the kringle 4 domains and to kringle 5 domain may be employed to assay levels of human apolipoprotein (a) in blood as a measure of risk of coronary heart disease.

8 Claims, 7 Drawing Sheets

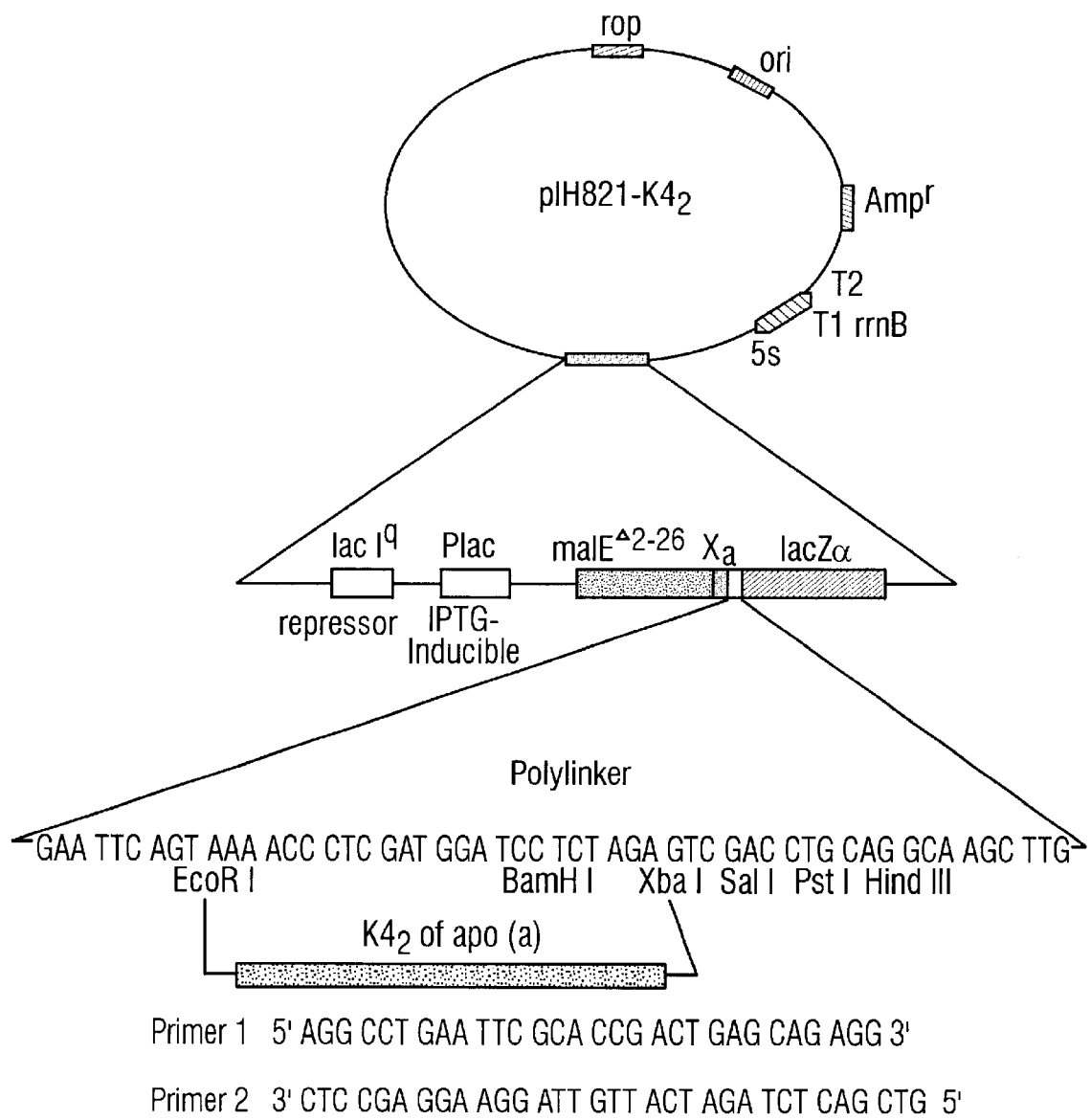
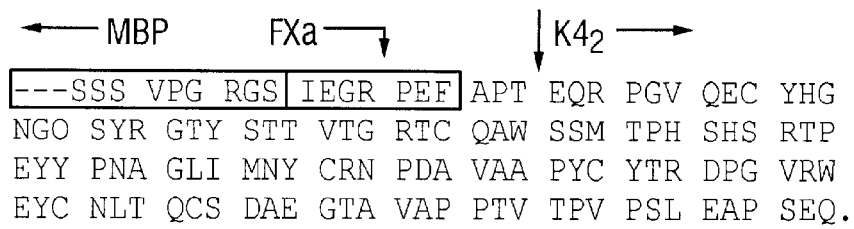
FIG. 2

EXPRESSION AND PURIFICATION OF KRINGLE DOMAINS OF HUMAN APOLIPOPROTEIN (A) IN *E. COLI*

This is a divisional of application Ser. No. 07/902,646 filed Jun. 23, 1992 now abandoned.

The United States Government has certain rights in the invention pursuant to the terms of grant no. NHLB1-18577 awarded by the National Institutes of Health.

BACKGROUND OF THE INVENTION

1. Field of the Invention

The invention relates to methods for the expression of human apolipoprotein(a) Kringle domains in bacterial cell hosts, to vectors useful for expression of the kringle domains and to the production of antibodies to human lipoprotein(a). Other aspects of the invention include methods of determining levels of serum lipoprotein(a) using these antibodies to define the antigenic distribution within the kringles 4 and 5 domains of human apo(a).

2. Description of Related Art

Human lipoprotein (a) has generated considerable interest because of its apparent correlation in blood with high risk of coronary heart disease (Scanu and Fless, 1990). Exactly how lipoliprotein (a) contributes to increased risk of heart disease is not known; however, according to some clinical studies, there appears to be a positive correlation between lipoprotein (a) blood levels and atherosclerosis. Lipoprotein (a) may favor the process of plaque buildup in the blood vessel wall. Indeed, lipoprotein (a) has been found at high levels in segments of coronary arteries after bypass surgery as well as in segments of peripheral vessels (Lawn, 1992).

Lipoprotein (a) is formed from the association of apo B100 and apolipoprotein (a) (apo (a) via a disulfide bond. Apo (a) is a large glycoprotein with extensive sequence homology to plasminogen (McLean, et al., 1987). Apo(a) exhibits size heterogeneity (300–800 KDa), the functional significance of which is not well understood. However, it is known that this size heterogeneity results from variation in the number of Kringle 4 domains in the molecule. Kringle 4 domains comprise on the average 78 amino acid residues with three highly conserved intramolecular disulfide bonds. It has been estimated that the number of Kringle 4-encoding repeats in the apo (a) gene can range from 9 to 35 (Lackner, et al., 1991). Kringle domains are so termed because of their resemblance to Danish pastries which have a comparable twisted structure (Lawn, 1992).

Kringle domains are found in other large proteins, most typically tissue plasminogen activator (Wilhelm, et al., 1990) and plasminogen (Mehnhart, et al., 1991). While there is extensive homology between apo (a) kringle $4_2$ and kringle 4 of plasminogen, there are significant differences in the amino acid sequences, potentially causing changes in function. It has been suggested that physiologically lipoprotein (a) may effect the transport of cholesterol to damaged vessels, thus delivering a material critical for cell repair. On the other hand, excess lipoprotein (a) at the vessel wall site may favor accumulation of material, leading to atherosclerotic plaque buildup (Lawn, 1992).

The Kringle 4 domains of apo (a) can be divided into 10 subtypes differing from plasminogen Kringle 4 by 12 to 23 amino acids (Morisett, et al., 1990). Like plasminogen, apo (a) shows high affinity for lysine-like ligands (Eaton, et al., 1987) and may also bind proline and hydroxyproline (Trieu, et al., 1991). However, the structural determinants of ligand binding for this protein are unknown. Individual Kringle domains appear to be independent structural units with autonomous functions (Trexler, et al., 1983). Kringle 2 of TPA and kringle 1 of plasminogen have been expressed in *E. coli* and found to bind to lysine, but kringle 4 and 5 domains from apo (a) have neither been expressed in *E. coli* nor characterized in specific binding properties.

In addition to kringle 4, apo (a) also contains a single Kringle 5 domain and a protease domain, both of which show high homology to the corresponding plasminogen domains (MacLean, et al., 1987).

Kringle domains of apo (a) may be the recognition sites for antibody binding. If such sites were identified, and were unique, a valuable method for specifically determining blood apo (a) levels would be available. At present, however, specific recognition sites on kringle 4 domains have not been identified and no truly immunospecific methods of determining apo (a) levels are available.

SUMMARY OF THE INVENTION

The present invention addresses one or more of the foregoing problems associated with the expression and purification of kringle apo (a) domains. The invention in particular includes the expression of recombinant kringle 4 and 5 domains from gram-negative bacteria, for example, *E. coli*. Recombinant kringle domains may be employed to generate antibodies which interact with apo (a) and lipoprotein (a). Such antibodies form the basis for various immunoassays designed to detect lipoprotein (a) and provide reproducible methods to detect this protein in human plasma.

One aspect of the present invention concerns the construction of an *E. coli* expression vector useful for producing recombinant kringle domains. These vectors include an inducible promoter sequence, a repressor gene sequence, a fusion protein and a polylinker gene sequence into which a DNA segment encoding a kringle polypeptide is cloned. The repressor gene is positioned upstream of an inducible promoter sequence which in turn is upstream of a selected fusion protein. The polylinker sequence is located between the fusion protein and the kringle polypeptide encoding DNA segments. The polylinker may be constructed with one or more restriction sites into which the kringle gene segment is inserted.

In preferred embodiments of the present invention, vectors incorporate maltose binding protein (MBP) as the fusion protein although other fusion partners might also be employed. MBP protein includes an amino acid sequence sensitive to $Fx_a$ protease. The expressed recombinant polypeptide includes three extraneous amino acids from the polylinker when the construct as shown in FIG. 1 is employed. MBP facilitates fusion protein isolation by virtue of its binding to amylose sepharose columns.

Kringle polypeptide expression has been demonstrated in *E. coli* but other prokaryotes or even eukaryotic host cells might be employed. Turning to the expression of the disclosed human apo (a) kringle polypeptides, once a suitable (full length if desired) clone or clones have been obtained, whether they be cDNA based or genomic, one may proceed to prepare an expression system for the recombinant preparation of the various regions or domains. The engineering of DNA segment(s) for expression in a prokaryotic or eukaryotic system may be performed by techniques generally known to those of skill in recombinant expression. It is believed that either eukaryotic or prokaryotic expression systems may be employed in the expression of kringle apo (a) domains; however, vector constructs useful for such expression have not been heretofore available, nor has a recombinant apo (a) kringle been successfully expressed in a gram negative host cell until the present invention.

Human apo (a) kringle 4 and 5 domains have now been successfully expressed in bacterial expression systems with the production of correctly folded structures. The cDNA for apo (a) kringle and kringle 5 domains has been separately expressed in *E. coli* systems, with the encoded proteins being expressed as fusions with maltose binding protein (MBP), a most preferred embodiment. Other fusion proteins with such fusion partners as β-galactosidase, ubiquitin, *Schistosoma japonicum* glutathione S-transferase, and the like are also envisioned. It is believed that bacterial expression has numerous advantages over eukaryotic expression in terms of ease of use and quantity of materials obtained thereby.

If, however, an eukaryotic expression system is chosen, it is believed that almost any eukaryotic expression system may be utilized for the expression of human apo (a) kringles, e.g., baculovirus-based, glutamine synthase-based or dihydrofolate reductase-based systems could be employed. However, in preferred embodiments, it is contemplated that vectors constructed analogously to pIH821, will be employed incorporating an origin of replication and an efficient eukaryotic promoter, as exemplified by the eukaryotic vectors of the pCMV series, such as pCMV5. Examples of host cells commonly employed with expression include 239, AtT-20, HepG2, VERO, HeLa, CHO, WI 38, BHK, COS-7, RIN and MDCK cell lines.

For expression in this manner, one would position the coding sequences adjacent to and under the control of the promoter. It is understood in the art that to bring a coding sequence under the control of such a promoter, one positions the 5' end of the transcription initiation site of the transcriptional reading frame of the protein between about 1 and about 50 nucleotides "downstream" of (i.e., 3' of) the chosen promoter.

Where eukaryotic expression is contemplated, one will also typically desire to incorporate into the transcriptional unit which includes the kringle-encoding DNA, an appropriate polyadenylation site (e.g., 5'-AATAAA-3') if one was not contained within the original cloned segment. Typically, the poly A addition site is placed about 30 to 2000 nucleotides "downstream" of the termination site of the protein at a position prior to transcription termination.

Whether employing a eukaryotic or a prokaryotic expression system, more than one kringle may be co-expressed in the same cell. This may be achieved by co-transfecting the cell with two distinct recombinant vectors, each bearing a copy of, for example, the kringle 4 or kringle 5-encoding DNA. Alternatively, a single recombinant vector may be constructed to include the coding regions for both domains, which could then be expressed in cells transfected with the single vector. In either event, the term "co-expression" herein refers to the expression of more than one kringle domain in the same recombinant cell.

As used herein, the term "engineered" or "recombinant" cell is intended to refer to a cell into which a recombinant gene, such as a gene encoding a kringle domain has been introduced. Therefore, engineered cells are distinguishable from naturally occurring cells which do not contain a recombinantly introduced gene. Engineered cells are thus cells having a gene or genes introduced through the hand of man. Recombinantly introduced genes will either be in the form of a cDNA gene (i.e., they will not contain introns), a copy of a genomic gene, or will include genes positioned adjacent to a promoter not naturally associated with the particular introduced gene.

Generally speaking, it is generally more convenient to employ as the recombinant gene a cDNA version of the gene. The use of a cDNA version will provide advantages in that the size of the gene will generally be much smaller and more readily employed to transfect or transform the targeted cell than will a genomic gene, which will typically be up to an order of magnitude larger than the cDNA gene. However, the inventor does not exclude the possibility of employing a genomic version of particular kringle genes where desired.

Where the introduction of a recombinant version of one or more of the foregoing genes is required, it will be important to introduce the gene such that it is under the control of a promoter that effectively directs the expression of the gene in the cell type chosen for engineering. In general, one will desire to employ a promoter that allows constitutive (constant) expression of the gene of interest. Commonly used constitutive promoters are generally viral in origin, and include the cytomegalovirus (CMV) promoter, the Rous sarcoma long-terminal repeat (LTR) sequence, and the SV40 early gene promoter. The use of these constitutive promoters will ensure a high, constant level of expression of the introduced genes. The inventor has noticed that the level of expression from the introduced gene(s) of interest can vary in different clones, probably as a function of the site of insertion of the recombinant gene in the chromosomal DNA. Thus, the level of expression of a particular recombinant gene can be chosen by evaluating different clones derived from each transfection or transformation experiment; once that line is chosen, the constitutive promoter ensures that the desired level of expression is permanently maintained. It may also be possible to use promoters that are specific for cell type used for engineering.

Monoclonal antibodies are prepared following in general the procedure of Goding (1980). This procedure is an immunization procedure using animals such as mice or rabbits. Purified kringle domains such as apo (a) $4_2$ or kringle 5 domains are combined with DNA cellulose or similar material and taken up in Freunds complete adjuvant for the initial immunization. Subsequent immunizations typically utilize incomplete Freunds adjuvant. BALB/C mice, for example, may be employed, with an initial intra-peritoneal immunization followed by intra-muscular injections. Blood samples are then periodically tested for the production of antibodies. High antibody titer animals are selected and the spleen is removed. Cells are isolated and tested for viability. Splenic lymphocytes are then fused with a non-secretor myeloma cell line such as $P_3$-NS1-AG4-1 obtained from a commercial source using PEG to induce cells to fuse. Cells are plated out and media then used for inducing culture growth, typically such media as HAT medium. After two or more clonings, cells may be weaned from the growth medium onto serum.

Preliminary screening for antibodies may be accomplished by an ELISA method. Hybridoma screening kits may be used, (for example, BRL, Bethesda, Md.). Plates are coated with goat serum and hybridoma culture supernatant is added to control plates and to plates which have been coated with one or more of the kringle polypeptides. After suitable incubation, plates are washed. Beta-galactosidase conjugated to goat anti-mouse antibody is diluted 1 to 200 in PBS containing 1% goat serum added and further incubated. A chromofluoric substance is next added, for example, p-nitrophenyl phosphate and incubation continued, typically for about 1 hour. This is followed by quenching, for example, with a sodium carbonate solution, and wells are then read at 410 nm on an ELISA plate reader. Positive reaction is indicated by the development of a yellow color in the well.

Cells are cloned from positive wells by plating at 0.5 to 2 cells per well with later recloning at 0.3 to 0.5 cells per well. Positive clones are recognized by screening methods similar to those used for the hybridomas. Isotyping of cells may be conveniently performed using immunoglobin subtype identification. Kits supplying antigens for coating the plates are commercially available, such as affinity purified goat antimouse IgG heavy and light chain. Typical dilutions employed are about 1:50. The second antigen will be a kringle antigenic polypeptide. Once the hybridoma cells are successfully cloned they may be grown in bulk. Antibody concentration might be expected to range from 10 to 100 micrograms per milliliter of culture solution.

One may also employ the disclosed recombinant kringle polypeptides as antigenic substances as inoculums to generate antisera. Antibodies and antibody compositions may be isolated from the serum of immunized animals such as, rats, mice, rabbits, etc. Antibodies, whether monoclonals or polyclonals, generated from antisera or generated through hybridoma technology as noted above may then be used in the development of various diagnostic procedures.

Purified kringle domains obtained by the methods herein described may be employed to generate antibodies that are specific for lipoprotein (a). Lipoprotein (a) is found in human serum and is commonly thought to be associated with risk of coronary disease. Monoclonal antibodies directed specifically to lipoprotein (a) are expected to provide the selectivity and sensitivity necessary for developing immunobased assays to detect this protein, with numerous variations and modifications of well-known general types of immunoassays possible. Preferred assay methods of the invention include various types of enzyme-linked immunosorbant acids commonly known as ELISAS and well-known to the art; however, it will be appreciated that the utility of monoclonal antibodies directed to lipoprotein (a) is not limited to this particular type of assay and that other useful embodiments include RIAs and other non-enzyme linked antibody-binding assays or procedures.

In preferred ELISA type assays, lipoprotein (a) or convenient fragments of lipoprotein A are immobilized onto a selected surface, preferably a surface exhibiting protein affinity, such as the walls of a polystyrene microtiter plate. After washing to remove incompletely adsorbed material, a non-specific protein such as bovine serum albumin (BSA) or casein may be used to provide a complete coating on the selected surface material. This coating material should be antigenically neutral with regard to the test antisera. This provides blocking of non-specific adsorption sites on the immobilizing surface and reduces background caused by non-specific binding of the anti-lipoprotein (a).

Once binding of lipoprotein (a) to the well surface is accomplished and after coating with the non-reactive material and washing to remove unbound material, the immobilizing surface is contacted with an antibody specific for lipoprotein (a). The contacting is performed in such a manner as to be conducive to immuno complex formation. In this case the formation of a complex will be between lipoprotein (a) and a monoclonal antibody which is directed to an epitopic region of that protein. Conditions which facilitate formation of these sorts of complexes preferably include diluting the antibody with diluents such as BSA, bovine gamma-globulin and phosphate buffered saline/Tween. These added agents tend to assist in the reduction of non-specific background. After contact, the mixture is typically allowed to incubate for about two to four hours, preferably at a temperature from about 25 to 27° C. Following incubation, the antibody antigen surface is washed in order to remove non-immuno complex material. A preferred washing procedure includes washing with solutions such as PBS/Tween or other appropriate buffers.

Following formation of specific immuno complexes between bound lipoprotein (a) and its monoclonal antibody and subsequent washing, the occurrence and amount of immuno complex formation may be determined by exposing the complex to a second antibody which has specificity for the first antibody. As the test sample will typically be of human origin, the second antibody will preferably be an antibody having specificity in general for human IgG. To provide detecting means, the second antibody will preferably have an associated enzyme that will generate color development upon incubation with an appropriate chromogenic substrate; thus, for example, one will desire to contact and incubate the antisera bound surface with a urease or peroxidase conjugated anti-human IgG for a period of time and under conditions which favor the development of immuno complex formation (e.g., incubation for two hours at room temperature in a PBS containing solution such as PBS/Tween).

After incubation with the second enzyme-tagged antibody and subsequent to washing for removing unbound material, the amount of enzyme label is quantified by incubation with a chromogenic substrate such as urea and bromocresol purple or a 2,2'-azino dye (3-ethyl-benzthiazoline-6-sulfonic acid ABTS and $H_2O_2$). In the case of peroxidase as the enzyme label, quantification is then achieved by measuring the degree of color generation, e.g., using a visible spectrophotometer.

As mentioned above, modification and changes may be made in the structure of apo (a) kringle polypeptides and still obtain a molecule having like or otherwise desirable characteristics. For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence (or, of course, its underlying DNA coding sequence) and nevertheless obtain a protein with like or even countervailing properties (e.g., antagonistic v. agonistic). It is thus contemplated by the inventors that various changes may be made in the sequence of kringle 4 or kringle 5 apo (a) proteins or peptides (or underlying DNA) without appreciable loss of their biological utility or activity.

In making such changes, the hydropathic index of amino acids may be considered. The importance of the hydropathic amino acid index in conferring interactive biologic function on a protein is generally understood in the art (Kyte et al., 1982). It is known that certain amino acids may be substituted for other amino acids having a similar hydropathic index or score and still retain a similar biological activity. Each amino acid has been assigned a hydropathic index on the basis of their hydrophobicity and charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant protein, which in turn defines the interaction of the protein with other molecules whether such molecules be enzymes, substrates, receptors, antibodies, antigens, and the like. It is known in the art that an amino acid may be substituted by another amino acid having a similar hydropathic index and still obtain a biological functionally equivalent protein. In such changes, the substitution of amino acids whose hydropathic indices are within ±2 is preferred, those which are within ±1 are particularly preferred, and those within ±0.5 are even more particularly preferred.

Substitution of like amino acids can also be made on the basis of hydrophilicity, particularly where the biological functional equivalent protein or peptide thereby created is intended for use in immunological embodiments. U.S. Pat. No. 4,554,101, incorporated herein by reference, states that the greatest local average hydrophilicity of a protein, as governed by the hydrophilicity of its adjacent amino acids, correlates with its immunogenicity and antigenicity, i.e., with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those which are within ±1 are particularly preferred, and those within ±0.5 are even more particularly preferred.

Amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine.

Another aspect of the invention involves the preparation of antigenic portions of apo (a) kringle domains. The antigenic kringles, or epitopes of the desired antigen, are selected and a gene encoding that antigen or epitope region is inserted into one or more of the recombinant vectors disclosed. Appropriate host cells are transformed and after screening for transformants, one is selected that expresses the antigen or part of the antigen for which an antibody is desired.

In immunodiagnostics, it is often possible and indeed more practical to prepare antigens from segments of a known immunogenic protein or polypeptide. Certain epitopic regions may be used to produce responses similar to those produced by the entire antigenic polypeptide. Indeed, the inventor has shown that antibodies prepared from kringle 4 of human apo (a) react with human lipoprotein (a). Often, however, responses to epitopic regions are not so strong as responses to the entire polypeptide. It is sometimes useful in enhancing immunogenic response, particularly when trying to generate antibodies, to incorporate the kringle polypeptide or fragment incorporating an epitopic region with another protein. The inventor has found, for example, that kringle 4 fusion protein combined with maltose binding protein generates a good antibody response when injected into an animal, for example, a mouse. Thus similar responses will be expected for kringle 5. Because the kringle 5 is a unique segment, in contrast with the multiple repeats of kringle 4, antibodies generated to it or to its epitopes will likely be highly selective to human lipoprotein (a).

BRIEF DESCRIPTION OF THE DRAWINGS

FIG. 1 shows the construction of the $E.$ $coli$ expression vector for apo (a) $K4_2$. The polylinker is SEQ ID NO:1; primer 1 is SEQ ID NO:2 and primer 2 is SEQ ID NO: 3.

FIG. 2 (SEQ ID NO:4) shows the partial sequence of expressed fusion protein Kringle 4 type 2/ maltose binding protein showing the C-terminal end of MBP, the FXa cleavage site, three vector-derived amino acid residues (PEF) and the complete amino acid sequence of apo (a) kringle 4 type 2 [derived from McLean et al. (1) and using the nomenclature of Morrissett et al. (11). Arrows indicate protease cleavage sites; FXa cleaves after IEGR and subtilisin A after APT.

DETAILED DESCRIPTION OF PREFERRED EMBODIMENTS

Figure 3:
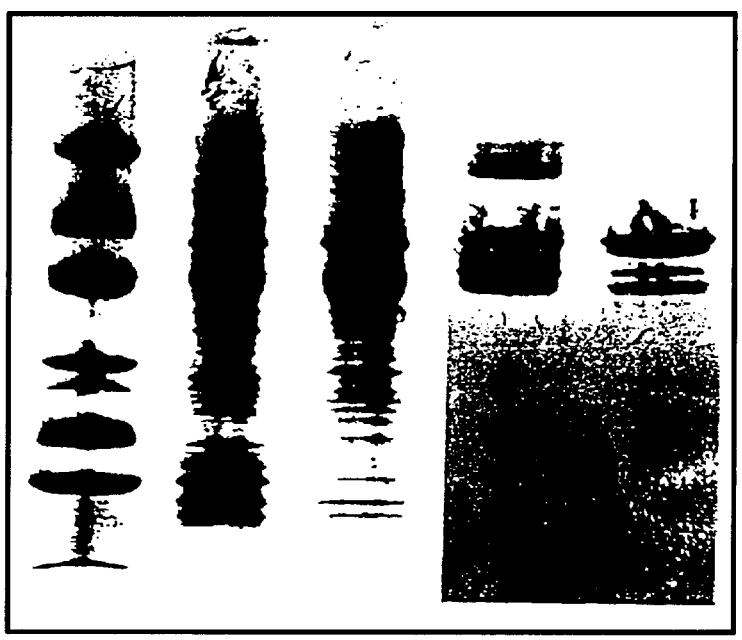
FIG. 3 shows the distribution of MBP and fusion protein in various fractions as determined by SDS-PAGE using 8–25% gradient polyacrylamide gels (Phast-gel system, Pharmacia). Lane, 1 molecular weight markers: phosphorylase B, 97000; BSA, 66200; ovalbumin, 45000; carbonic anhydrase, 30000; soybean trypsin inhibitor, 21500; and lysozyme, 14400. Lane 2, whole cell lysate (4 μg). Lane 4, fraction of whole cell lysate with affinity for amylose-agarose (2 μg). Lane 5, fusion protein isolated by affinity chromatography on anti apo (a)-Sepharose (1 μg). Gel was stained with Coomassie blue R250.
Figure 4:
FIG. 4 shows the proteolytic release of $K4_2$ from the fusion protein-MBP mixture obtained by amylose-agarose affinity chromatography. Hydrolysates were analyzed by SDS-PAGE using 4–30% acrylamide gradient gels (Pharmacia). The amount of protein applied to lane 1 is 10 μg and 15 μg to lanes 2–7. Cleavage with 1% w/w FXa for 24h at 22° C. (lane 1); cleavage with 0.5% (w/w) trypsin for 5h at 22° C. (lane 2) and 24h at 22° C. (lane 3); cleavage with 10% (w/w) pancreatic elastase for 5h at 22° C. (lane 4) and 24h at 22° C. (lane 5); cleavage with 0.1% (w/w) subtilisin A for 5h at 22° C. (lane 6) and 24h at 220C. (lane 7). Lane 8 contains the same molecular weight markers (10 μg/band) as shown in FIG. 3. Lane 1 is a "Western" blot developed with anti apo (a) and $^{125}$I-labeled goat anti rabbit IgG followed by autoradiography with Kodak XAR film. Lanes 2–8 are stained with Coomassie blue R250.
Figure 5A:
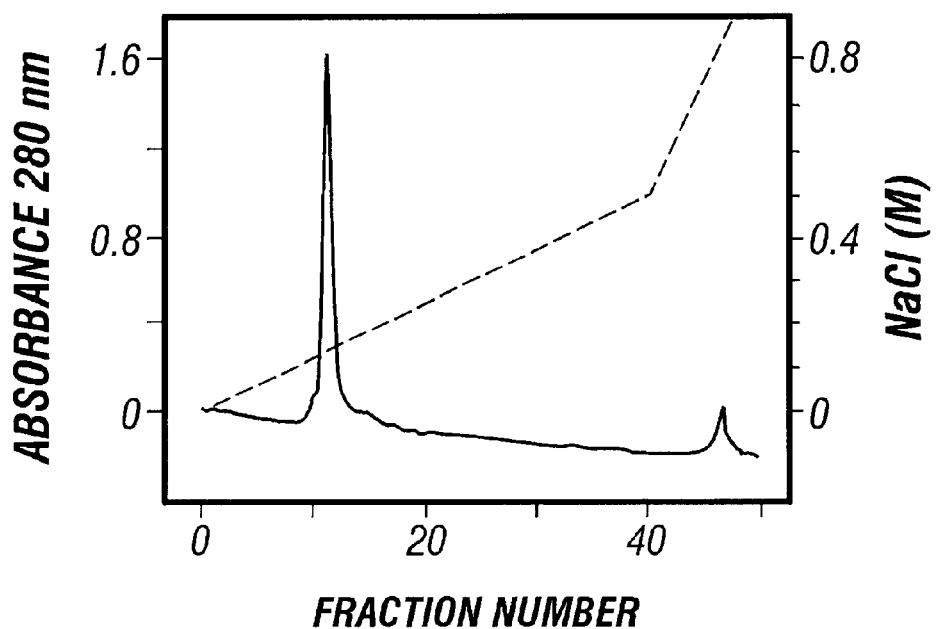
FIG. 5 shows the isolation of $K4_2$ from the subtilisin A hydrolysate of the MBP-fusion protein mixture by FPLC using a MONO-Q column (Pharmacia). Panel A, 0.5 mg of hydrolysate dialyzed vs 10 mM TRIS, 0.01% $NaN_3$, pH 7.4 was applied to the column at flow rate of 1 ml/min at 4° C. Elution was achieved with a 20 min. gradient of 0 to 0.5 M NaCl in 10 mM TRIS, 0.01% $NaN_3$, pH 7.4. Panel B, 5 mg hydrolysate in 20 mM ethanolamine, 0.01% $NaN_3$, pH 9.5 was applied to the column at a flow rate of 1 ml/min. $K4_2$ was separated from MBP with a 20 min gradient ranging from 0 to 0.3 M NaCl in 20 mM ethanolamine 0.01% $NaN_3$, pH 9.5. Fractions containing $K4_2$ were immediately adjusted to pH 7.4 with 1 M acetic acid.
Figure 5B:
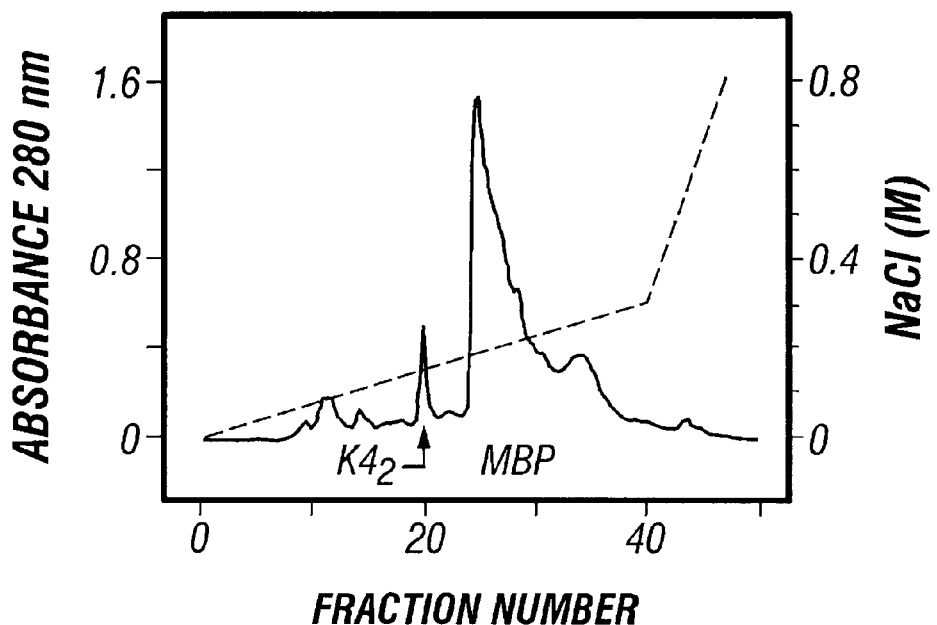
Figure 6:
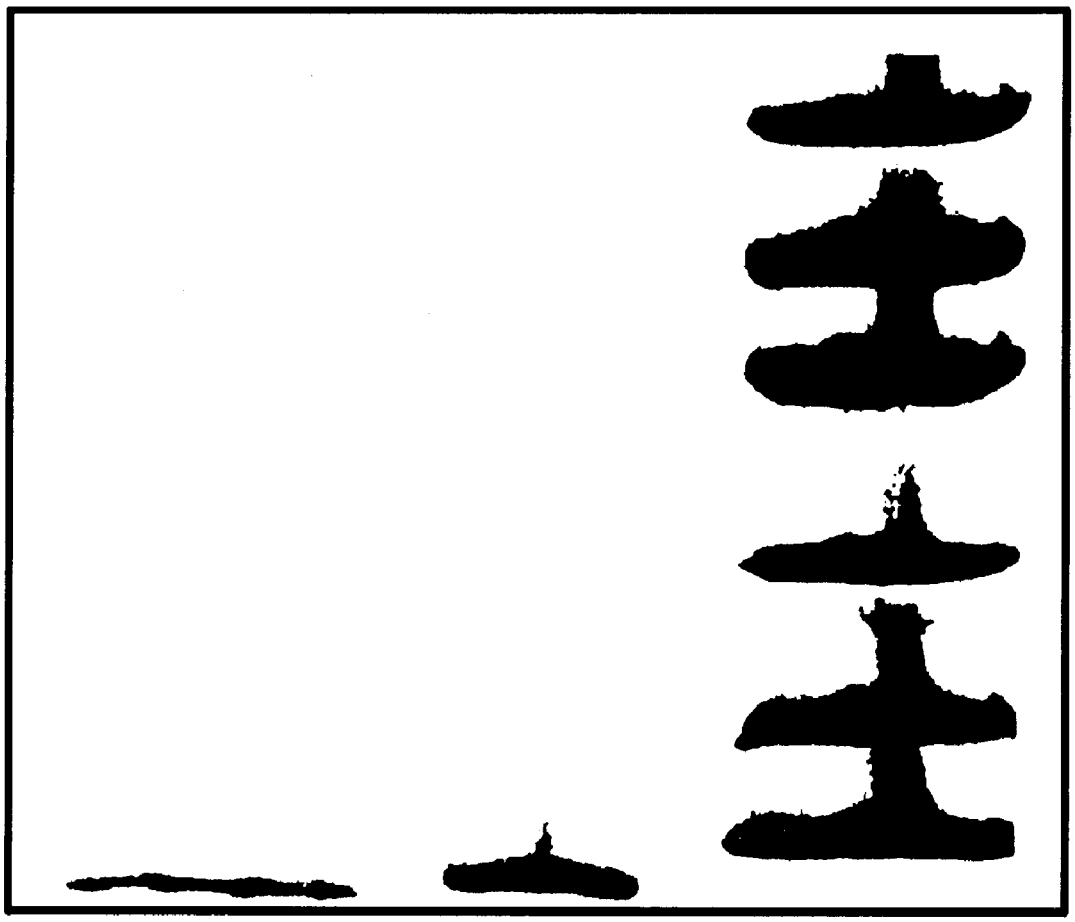
FIG. 6 shows the characterization of purified $K4_2$ by SDS-PAGE using 8–25% polyacrylamide gels (Phast-gel system, Pharmacia). Lane 1, 0.6 μg $K4_2$; Lane 2, 0.6 μg $K4_2$ reduced with 5% mercaptoethanol; Lane 3, same molecular weight markers (2 µg/band) as in FIG. 3.
Figure 7:
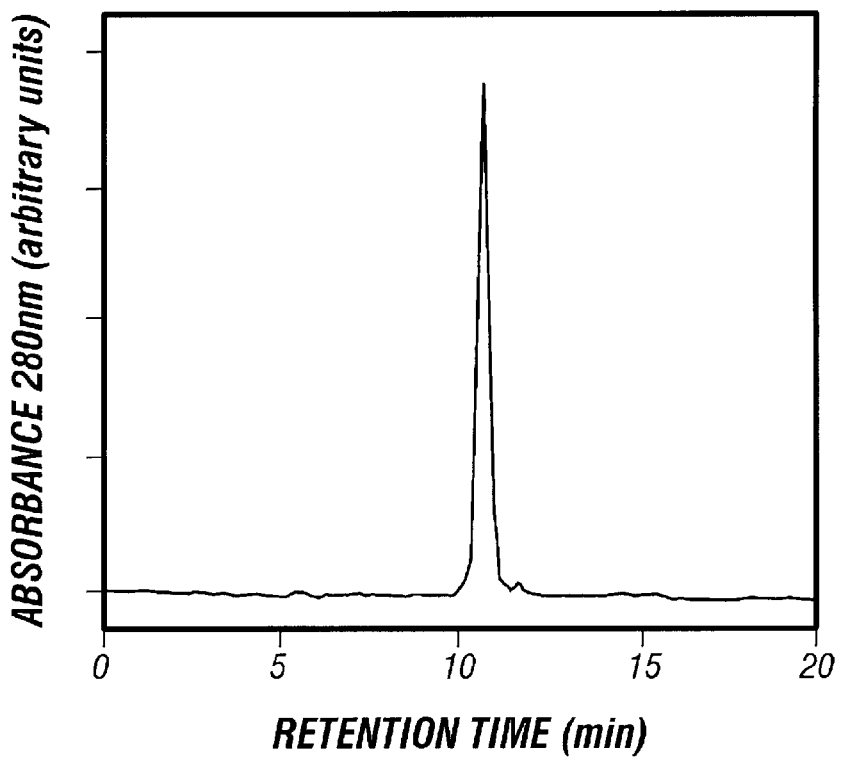
FIG. 7 shows the characterization of purified $K4_2$ by HPLC using a ToyoSoda TSK gel G 3000 SW column (7.5 mm×30 cm) at a flow rate of 1 ml/min. $K4_2$ was dialyzed against 10 mM phosphate, 150 mM NaCl, 0.01% $NaN_3$, pH 6.7 and injected into the column in a volume of 20 µl at a concentration of 1 mg/ml.

The present invention is the first expression of a recombinant apo (a) kringle domain in *E. coli* that does not have the ability to bind to lysine-Sepharose. Apolipoprotein (a) or apo (a) consists of a unique kringle 5 domain and up to 37 kringle (K) 4 domains that are homologous to those of plasminogen. Unlike the plasminogen kringles, however, the human apo (a) kringles expressed from *E. coli* as herein disclosed do not bind to lysine and also differ structurally to the extent they are glycosylated. However, the human apo (a) protein binds to lysine, fibrin(ogen), and to plasminogen binding sites on endothelial cells and other blood cells.

The K4 domains of apo (a) can be classified into 11 different types, with the second type (K4-2) occurring up to 28 times in the protein. Kringle 5 domain, in contrast with kringle 4 domains, is unique in the apo (a) molecule. The successful expression of kringle 5 and kringle 4 in *E. coli* provides the basis for obtaining antibodies to develop sensitive and selective assays for lipoprotein (a), the presence of which in human serum is thought to indicate relative risk of coronary disease.

In the examples provided herein, apo (a) kringles are expressed in *E. coli* fused with maltose binding protein. This fusion partner takes advantage of ability to bind with, for example, amylose agarose supports. This was a provident choice because the recombinant apo (a) kringle domains, in contrast to kringle 1 and 2 domains in plasminogen, bind neither with lysine nor proline and are not therefore readily purified by chromatography on supports incorporating lysine or proline as binding sites.

The pIH821 vector employed to construct the expression vector of the present invention included the malE gene without its signal sequence. The FXa (factor $10_a$) cleavage site which is part of this gene, was retained when the recombinant clone comprising the DNA for the apo (a) kringle domains was constructed. Although the introduction of proline adjacent to the arginine in the FXa cleavage site precluded the use of factor $10_a$ enzyme in the production of apo (a) kringles, other proteases were effective in clipping the kringle domain from the fusion protein. N-terminal sequencing showed that subtilisin A released $k4_2$ from the fusion protein without the first three amino acid residues of the leading linkage peptide. This created a recombinant protein without vector derived amino acids but with an intact kringle that included the characteristic cysteine residues.

Several lines of evidence indicated that the kringles were properly folded, including (1) the lower mobility of SDS-PAGE reduced kringle compared with unreduced kringle; (2) absence of free sulfhydryls; (3) changes in aromatic amino acid fluorescence spectra upon denaturation; and (4) specific interaction of the expressed kringles with monoclonal antibodies specific for apo (a).

The apo (a) kringles of the present invention appear to be correctly folded, despite the fact that they do not bind to lysine or proline, as do some of their homologous kringle counterparts in plasminogen and TPA. Apo (a) kringle $4_2$, after deanturation and oxidative renaturation, did not bind to lysine-Sepharose, nor did kringle $4_2$ purified from *E. coli* periplasmic space show lysine affinity. In contrast, reduced plasminogen kringle 4 spontaneously refolds and correctly reoxidizes its three disulfide bonds with a half-life of 3 h (Trexler and Patthy, 1983). Assuming the apo (a) kringles also properly refold under the same conditions, it is likely that, at least in the case of apo (a) kringle $4_2$, failure to bind to lysine Sepharose may be the substitution of valine for asp 56, thus altering the anionic center of the ligand binding pocket.

The importance of ionic interactions in the binding of the lysine-like ligand e-amino caproic acid to plasminogen kringle 4 is indicated by recent crystallographic studies. These studies indicate that the lysine binding site consists of doubly charged anionic and cationic centers which are formed by asp 54/asp 56 and lys 35/arg 69 and a nonpolar trough consisting of trp 60, phen 62 and trp 70 (Mulichak et al., 1991; Wu, et al., 1991). However, unlike the replacement of valine for asp 56 which weakens the anionic center, the other substitutions, e.g., arginine for lys 35 and tyrosine for trp 60 and phe 62, are conservative and may not significantly affect ligand binding.

Lysine binding may be affected by the glycosylation of apo (a) kringles, another difference between plasminogen kringles and apo (a) kringles, the former not being glycosylated. Glycosylation, a difference in amino acid composition resulting in tertiary structure differences may account for the distinguishable properties of human apo (a) kringles compared with the kringles of human plasminogen.

Materials

Restriction endonucleases were from New England Biolabs (Beverly, Mass.). DNAse I was from Boehringer-Mannheim; trypsin TPCK was from Worthington Diagnostic Systems; porcine pancreatic elastase was from Calbiochem;

and subtilisin A was from Miles Laboratories (Naperville, Ill.). Amylose-agarose was from New England Biolabs, lysine-Sepharose and proline-agarose were from Sigma (St. Louis, Mo.). All other reagents were reagent grade purchased from Sigma.

Escherichia coli expression strain PR722 was purchased from New England bioLabs. Apo (a) clone pUC119λα41 was obtained from J. W. McLean (Genentech, Inc., San Francisco). pIH821 is available from commercial sources.

Methods

Amino-terminal Sequence Analysis

Sequence analysis was performed by Dr. L. R. Riviere (Genetics Institute, Andover, Mass.). $K4_2$ at a concentration of 2.5 µg/50 µl in 137 mM NaCl, 2.7 mM KCl, 4.3 mM $Na_2HPO4$ and 1.4 mM $KH_2PO_4$, pH 7.4 was loaded onto an Applied Biosystems automated pulsed liquid protein sequencer (Hewick, et al., 1981) and as optimized for subpicomole PTH analysis (Tempst and Rivere, 1989). Sequentially removed phenylthiohydantoin amino acids were identified using an on-line Applied Biosystems 120A HPLC. $K4_2$ was reduced and pyridylethylated on the sequencer (Kruft, et al., 1991).

Electrophoresis

SDS-PAGE was carried out with the Pharmacia Phast-gel system using 8–25% gradient polyacrylamide gels. The gels contained 0.112M acetate and 0.112M TRIS, pH 6.4; the buffer strips contained 0.20M tricine, 0.20M TRIS, and 0.55% SDS, pH 7.5. Alternatively SDS-PAGE was conducted with precast 4–30% gradient polyacrylamide gels (Pharmacia). Gels of both systems were stained either with Coomassie Blue or with silver. For blotting experiments, phast gels were pressure blotted to Immobilon P membranes (Millipore) for 16 h, blocked with 4% BSA, exposed to rabbit anti human apo (a), followed by $^{125}$I-labelled goat anti rabbit IgG (ICN Biomedical). The membranes were placed on Kodak XAR film for 16 to 48 hr at room temperature.

Molecular Weight Determination

The molecular weight of $K4_2$ was determined by SDS-PAGE. The molecular weight markers used were: phosphorylase B, 97,000; BSA, 66,200; ovalbumin, 45,000; carbonic anhydrase, 30,000; soybean trypsin inhibitor, 21,500; and lysozyme, 14,400. The molecular weight of $K4_2$ was also determined by gel filtration in 10 mM phosphate, 150 mM NaCl, 0.01% $NaN_3$, pH6.7 using an IBM LC/9533 HPLC system equipped with a Perkin Elmer LC/85 detector set at 220 nm. A ToyoSoda TSK gel G 30000 SW column (7.5 mm×30 cm) was used at a flow rate of 1 ml/min. Molecular weight markers and $K4_2$ were injected into the column in a volume of 20 µl at a concentration of 1 mg/ml. Molecular weight markers used were: BSA, 66,200, ovalbumin, 45,000; carbonic anhydrase, 30,000; soybean trypsin inhibitor, 21,5000; and cytochrome C 12,400. The void volume was determined with blue dextran.

Spectroscopic Methods

Fluorescence spectra were obtained with 280 nm excitation using a Photon Technology International Alphascan spectrofluorometer. Spectra were obtained at a scan rate of 1 nm/sec and a spectral bandpass of 5 nm.

Optical spectra were obtained with a Cary 14 Uv-Vis spectrophotometer interfaced to an IBM PC-compatible computer for data acquisition and storage (OLIS, Jefferson, Ga.). The data acquisition parameters were according to Sherman, et al. (1991). For each sample the absorption spectrum was collected five times and the average of the five scans was stored.

4,4'-dithioldipyridine (Aldrithiol-4) was purchased from Aldrich. $K4_2$ or K5 was reacted with this reagent according to Copeland, et al., 1991.

Competitive ELISA

Polystyrene microtiter plates (Beckman) were coated overnight at room temperature with 100 µl, 4 µg/ml affinity purified goat anti human apoB100. After blocking for 1h with 1% BSA in 10 mM TRIS, 150 mM NaCl, 0.01% thimerosal, pH 7.4, the plates were incubated with 100 µl of a saturating concentration of 1p(a) (6.25 µg/ml) for 2 h at room temperature. After three washes with 0.1 M $NaHCO_3$, 0.5 M NaCl, 0.1% BSA, 0.1% Tween 20, pH 8.1, serial dilutions of $K4_2$ in a volume of 100 µl were added, followed by 100 µl of MAb 1E1 or 4D2, both at a concentration of 0.63 µg/ml. The plate was incubated for 1.5 h at room temperature on an oscillating minishaker (Dynatech) set at level 3. After three more washes the plate was incubated with goat antimouse IgG-alkaline phosphatase at a dilution of 1:8000 for 1h at room temperature and washed three additional times. Color development proceeded with 100 µl of 1 mg/ml disodium p-nitrophenyl phosphate in 10% (w/w) diethanolamine, 0.01% $MgCl_2$, pH 9.8 for 30 min at room temperature in the dark. Color development was stopped with 100 µl 1 N NaOH. Absorbance was measured at 405 nm.

The following examples are intended to illustrate the practice of the present invention and are not intended to be limiting. Although the invention is demonstrated with apo (a) kringle 4 and kringle 5, other apo (a) kringles, whether fragments or functionally equivalents could be expressed in a similar manner. The recombinant kringles, expressed for the first time from recombinant E. coli, are useful in generating antibodies with specificity toward lipoprotein (a). Numerous assays, based on methods known to those of skill in the art, could be developed employing any one or more of monoclonal antibodies directed to particular epitopic regions of the apo (a) kringle domains.

EXAMPLE 1

Kringle domains are common features of the large protein apo (a). Many of these domains do not have a clearly defined function, yet one or more may be significantly involved in ligand binding. Additionally, epitopic regions of these domains are potential immunogens useful in generating monoclonal antibodies to apo (a). The following example illustrates the cloning of a typical Kringle domain, Kringle 4 type 2 domain, into a maltose binding protein vector plasmid to obtain an expression vector which directs synthesis of large quantities of fusion protein in the host cell.

Expression Vector for Kringle 4 Type 2 Domain

An apo (a) clone, pUC119λα41, contained apo (a) cDNA encompassing the domain starting with the 26th Kringle through the C-terminal including the 3' untranslated region, sequence shown in McLean, et al. (1987). The apo (a) $K4_2$ CDNA was amplified by PCR using as upstream primer 5'-AGGCCTGAAT TCGCACCGAC TGAGCAGAGG-3' (SEQ ID NO:2) and as downstream primer 5'-GTCGACTCTA GATCATTGTT CGGAAGGAGC CTC-3'SEQ ID NO:5.

Both primers were prepared with a model 380A DNA Synthesizer (Applied Biosystems). The upstream primer contained the initial six codons of the identical apo (a) $K4_2$ cDNA and its 5' end included a cloning site for EcoRI. The downstream primer contained the final six codons of the identical apo (a) $K4_2$ cDNA and included a stop codon and a cloning site for XbaI. Using a GeneAmp PCR reagent kit with Amplitaq DNA polymerase and a DNA Thermal Cycler (Perkin-Elmer/Cetus), PCR amplification was performed (Hummel, et al., 1990). Ten nanograms of apo (a) fragment from plasmid pUC119λα41 was used as a template. Following denaturation of the DNA at 94° C. for 5 min., the amplification was carried out for 25 cycles as follows: annealing at 60° C. for 2 min., polymerization at 72° C. for 2 min. and denaturation at 94° C. for 1 min. The PCR products of the appropriate size were cut from 3% Nusieve GTG agarose gel (FMC BioProducts, Rockland, Me.) which was melted at 65° C. for 20 min in a buffer containing 0.3 M NaCl, 20 mM Tris, 1 mM EDTA and 0.1% SDS, pH 7.5. The PCR products were purified by phenol extraction and ethanol precipitation, digested with EcoRI and XbaI, reextracted with phenol and then re-precipitated with ethanol.

The pIH821-$K4_2$ vector was constructed by first selecting EcoRI and XbaI as cloning sites in order to limit the number of additional amino acids between the $FX_a$ cleavage site and the 5' terminal of $K4_2$. The maltose binding protein vector, pIH821, was digested with EcoRI AND XbaI and the resulting linear DNA fragment was recircularized by ligation with the applied apo (a) $K4_2$ products. The recombinant clone apo (a) pIH821-$K4_2$ was digested with KpnI and SalI at sites located upstream of the EcoRI cloning site and downstream of the Xba I cloning site, respectively. The resulting fragment, containing the linkage region with the FXa cleavage site and the apo (a) $K4_2$ CDNA was purified, trimmed and cloned into SmaI-digested M13mp10 DNA to check the inserted sequence and reading frame of the pIH821-$K4_2$ vector. DNA sequencing was carried out by the dideoxynucleotide termination method (Sanger et al. (1980).

EXAMPLE 2

The unique kringle 5 domain of apo (a) was expressed in *E. coli* using methods according to Example 1.

Expression Vector for Kringle 5 Domain cDNA for the Kringle 5 domain of apo (a) was contained in the apo (a) clone, pUC119λα41 (McLean, et al., 1987). The unique Kringle 5 is located at position 4204–4294 from the N-terminal end of apo (a). cDNA encoding kringle 5 was amplified by the polymerase chain reaction using as upstream primer 5'-ACTACGCCTG AATTCCCTTC TGAACAAGA CTGT-3' SEQ ID NO:6 and as downstream primer 5'-GCCAGGCGCT CTAGATTAAT CAAAT-GAAGA GGATGC-3' SEQ ID NO:7.

Kringle 5 DNA was cloned into maltose binding vector pIH821 in a manner analogous to the procedure for Kringle 4, type 2, according to Example 1.

EXAMPLE 3

Employing the vectors according to Example 1 or Example 2, fusion proteins comprising Kringle domains were readily expressed in transformed host cells. In the example following, fusion proteins were secreted into the periplasmic space and also found associated with the soluble cytosolic fraction when expressed in *E. coli* PR722.

Expression of $k4_2$MBP Fusion Protein

After transformation of *E. coli* PR722 with the apo (a) $K4_2$-pIH821 vector, the "$P_{tac}$" promoter was activated by growing the cells in a medium with IPTG. Five ml of a transformed overnight culture were inoculated into 500 ml medium, supplemented with ampicillin 100 μg/ml. The inducer IPTG was added to a final concentration of 0.3 mM until the turbidity of the medium at 600 nm reached an optical density of 0.6. The cells were harvested by centrifugation after another two hours of incubation.

The kringle polypeptide was expressed as a fusion protein with the maltose binding protein (MBP). The fusion protein was expressed without a signal sequence, the majority associated with the soluble cytosolic fraction (75%) and the remaining 25% was secreted into the periplasmic space.

EXAMPLE 4

While several methods may be useful in isolating fusion proteins after expression in host cells, two methods, described in this example, provided good yields of fusion protein, and ultimately, apo (a) kringle proteins. Fusion proteins were isolated either by lysis or cold osmotic shock techniques. Separation of the kringle protein from its fusion partner was effected by proteolytic cleavage followed by anion exchange chromatography.

Isolation of Fusion Protein

Frozen cells were thawed and or fresh cells were treated for 20 min at room temperature with 10 ml per g wet cells lysis buffer that contained 0.2 mg/ml lysozyme dissolved in 50 mM TRIS-HCl, 75 mM NaCl, 1 mM $Na_2$ EDTA, 1 mM $Na_2$ EGTA, 0.2 mM PMSF, pH 7.5. The mixture was then incubated with DNAse I at a final concentration of 0.01 mg/ml for 30 min at 37° C. Complete cell lysis was achieved by ultrasonication. Upon centrifugation at 10,000 g for 20 min at 4° C., the supernatant was applied to an amylose agarose affinity column (2.5×10 cm) at a flow rate of 20 ml/h. The column was washed with 10 mM phosphate, 0.5 M NaCl, 1 mM $Na_2$EGTA, 0.02% $NaN_3$, pH 7.0 until the absorbance at 280 nm reached baseline values. The fusion protein, together with contaminating MBP, was eluted with 10 mM maltose dissolved in the wash buffer.

The fusion protein was also prepared from the periplasmic fraction of cells subjected to cold osmotic shock (Neu and Heppel, 1965). Cells were harvested by centrifugation at 4° C. and 10,000 g for 20 min. The pellet was resuspended in 80 ml 30 mM TRIS/HCl, 20% sucrose, 1 mM EDTA, pH 8.0 per gram cells wet weight and incubated 5–10 min. Following centrifugation at 4° C. the supernatant was removed and the pellet was resuspended in 80 ml/gm cells ice-cold 5 mM $MgSO_4$ and incubated for 10 min with shaking on ice. The shocked cells were centrifuged for 20 min at 10,000×g and the cold osmotic shock fluid was removed and dialyzed against 10 mM phosphate, 0.5 M NaCl, 1 mM $Na_2$ EGTA, 0.02% $NaN_3$, pH 7.0. The fusion protein was then purified by amylose agarose affinity chromatography using a column (2.5×10 cm) at a flow rate of 20 ml/hr. The column was washed with 10 mM phosphate, 0.5 M NaCl, 1 mM $Na_2$EGTA, and 0.02% $NaN_3$ pH 7.0 until the absorbance at 280 nm reached baseline values. The fusion protein, together with MBP was eluted with 10 mM maltose dissolved in the wash buffer.

Proteolytic Cleavage of Fusion Protein

The mixture containing the fusion protein and MBP was dialyzed against 10 mM TRIS, 0.15 M NaCl, 0.01% $NaN_3$, pH 8.0. Cleavage of the fusion protein was then initiated with FXa using methods outlined by New England Biolabs in their protocol for MBP vectors.

Proteolysis of the fusion protein with FXa was ineffective, Other proteolytic enzymes were investigated ability to release $K4_2$ from the fusion protein. The proteolytic enzymes used were: N-tosyl-L-phenylalanine chloromethyl ketone treated trypsin, porcine pancreatic elastase and subtilisin A (*Bacillus licheniformis*). Of these, subtilisin A was most effective. Hydroysis of the mixture (0.5 to 1.0 mg/ml protein) containing MBP and fusion protein dissolved in 10 mM TRIS, 0.15 M NaCl, 0.01% $NaN_3$, pH 8.0 was conducted as a function of time at varying ratios of enzyme to protein at room temperature. The reaction was stopped by the addition of PMSF (2 mM final concentration).

Isolation of $K4_2$

The digestion mixture was dialyzed overnight at 4° C. against 100 volumes of 20 mM ethanolamine, 0.01% $NaN_3$, pH 8.0. Upon dialysis, the pH of the mixture was adjusted to pH 9.5 with 1 N NaOH and $K4_2$ was purified by chromatography using a Pharmacia FPLC dual pump system equipped with a flow cell monitor and chart recorder. A Mono-Q HR 5/5 anion exchange column was used and was equilibrated in the same buffer. Up to 10 mg protein was injected into the column using a 10 ml super loop. $K4_2$ was eluted from the column which was monitored at 280 nm at a flow rate of 1 ml/min using a 20-min linear gradient ranging from 0–0.3 M NaCl in 20 mM ethanolamine, 0.01% $NaN_3$, pH 9.5. Fractions containing the pure $K4_2$ were immediately adjusted to pH 7.4 with a predetermined amount of 1N acetic acid and dialyzed against 10 mM phosphate, 0.15M NaCl, 0.01% $NaN_3$, pH 7.4.

Yields of kringle $4_2$ so isolated using subtilisin A cleavage and the above herein described chromatography was 170±30 μg/g wet cells. The product was monomeric as judged by size exclusion chromatography, and intact with only the first three amino acid residues of the leading flanking peptide missing, as shown by N-terminal sequence analysis.

EXAMPLE 5

Kringle 4 protein cleaved from its fusion partner, maltose binding protein (MBP), did not bind to a lysine-Sepharose support. The following procedure showed that apo (a) bound readily to a lysine-containing support but kringle 4 domain showed no lysine affinity.

Lysine-Sepharose Binding of Apo (a) and Kringle 4

$K4_2$ (0.2 mg/ml) in 10 mM TRIS, 0.15 M NaCl, and 0.01% $NaN_3$, pH 7.4 was reduced with 20 mM DTT at 37° C. for 1h, made 1M in TRIS pH 8.0 and alkylated with 60 mM iodoacetic acid for 1h in the dark followed by dialysis against 10 mM TRIS, 0.15 M NaCl, 0.01% $NaN_3$, pH 7.4. $K4_2$ and other proteins were dialyzed against 10 mM phosphate, 0.15 M NaCl, 0.01% $NaN_3$, pH 7.4, and applied to a lysine-Sepharose column (0.5×5 cm) which was equilibrated with the same buffer at a flow rate of 10 ml/h. The column was monitored at 280 nm using an Altex model 150 UV monitor equipped with a Kipp-Zonen model BD 41 chart recorder. The column was washed with the same buffer until the absorbance reached baseline values. Bound material was eluted with 200 mM trans-4-aminomethyl cyclohexanecarboxylic acid in 10 mM phosphate, 0.15 M NaCl, 0.01% $NaN_3$, pH 7.4. Proline-agarose chromatography of $K4_2$ was conducted under identical conditions.

Figure 11A:
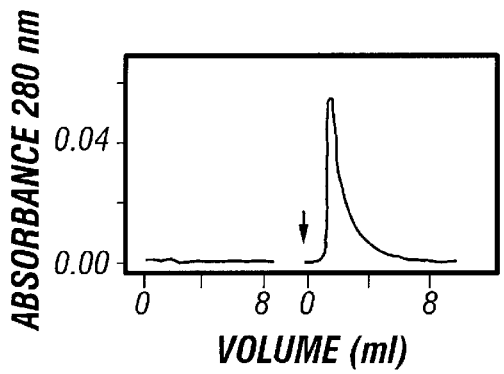
FIG. 11 is a lysine-Sepharose and proline-agarose chromatogram of $K4_2$. Approximately 100 µg of each protein was applied to a 1 ml lysine-Sepharose (panels A-D) or proline-agarose column (panels E and F) in 10 mM phosphate, 150 mM NaCl, 0.01% $NaN_3$ pH 7.4 at a flow rate of 10 ml/h. Bound proteins were eluted from the lysine-Sepharose column with 200 mM trans-4-aminomethyl-cyclohexane carboxylic acid dissolved in the above buffer. The eluant for proteins bound to proline-agarose was 200 mM proline in the above buffer. Panel A, Lp(a); panel B, $K4_2$; panel C, denatured and reoxidized $K4_2$; panel D, lysozyme; panel E, Lp(a); and panel F, $K4_2$. The arrows indicate the start of elution.
Figure 11D:
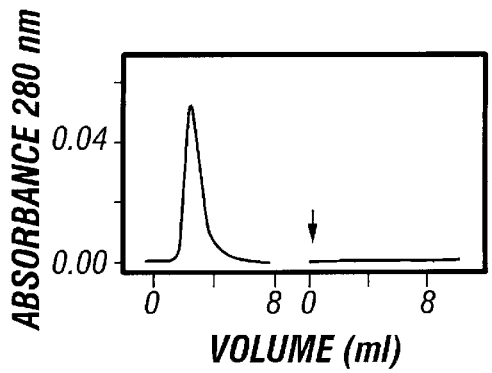
Figure 11B:
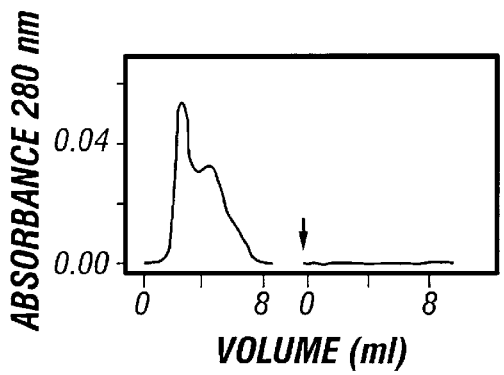
Figure 11E:
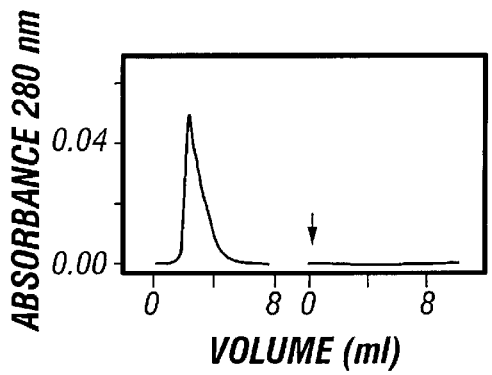
Figure 11C:
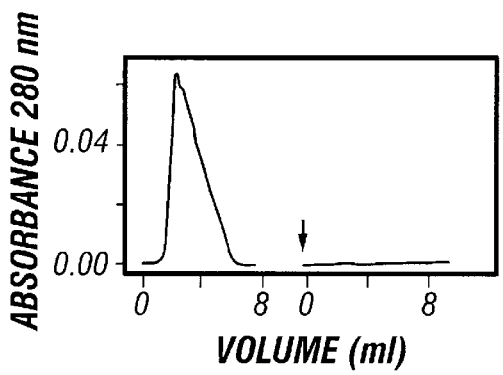
Figure 11F:
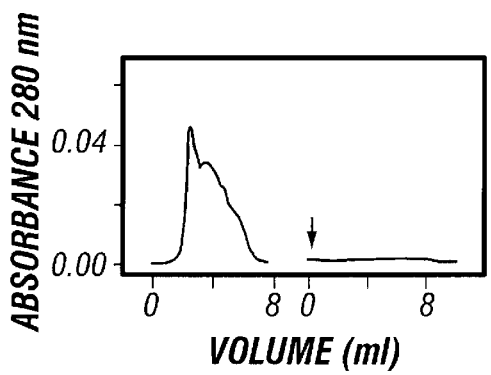

Lipoprotein (a) bound well to the lysine Sepharose and was readily eluted with EACA, as shown in FIG. 11A. In contrast, $K4_2$, either before or after GuHCl denaturation and oxidative refolding (FIGS. 11B and 11C, respectively) did not bind. $K4_2$ did not bind regardless of its source from whole cell lysate or periplasmic space. The trailing aspect of the FIGS. 11B and 11C chromatogram was not caused by a weak affinity of this protein for the lysine-Sepharose since a similar curve was obtained in the presence of 200 mM EACA. Lysozyme, similar in size to $K4_2$, did not bind to the support, as indicated in FIG. 11D. Neither lipoprotein (a) nor $K4_2$ had an affinity for lysine-Sepharose resin.

EXAMPLE 6

It was important to assess the three dimensional structure of isolated kringle 4 and 5 domains to determine if the protein was expressed in correctly folded form. This was done by determining tryptophan environment, solvent exposure of the aromatic amino acids, cysteine residue reactivity and monoclonal antibody activity. These results showed that the kringle $4_2$ peptide was correctly folded.

Determination of Kringle 4 Folding

Fluorescence

Figure 8:
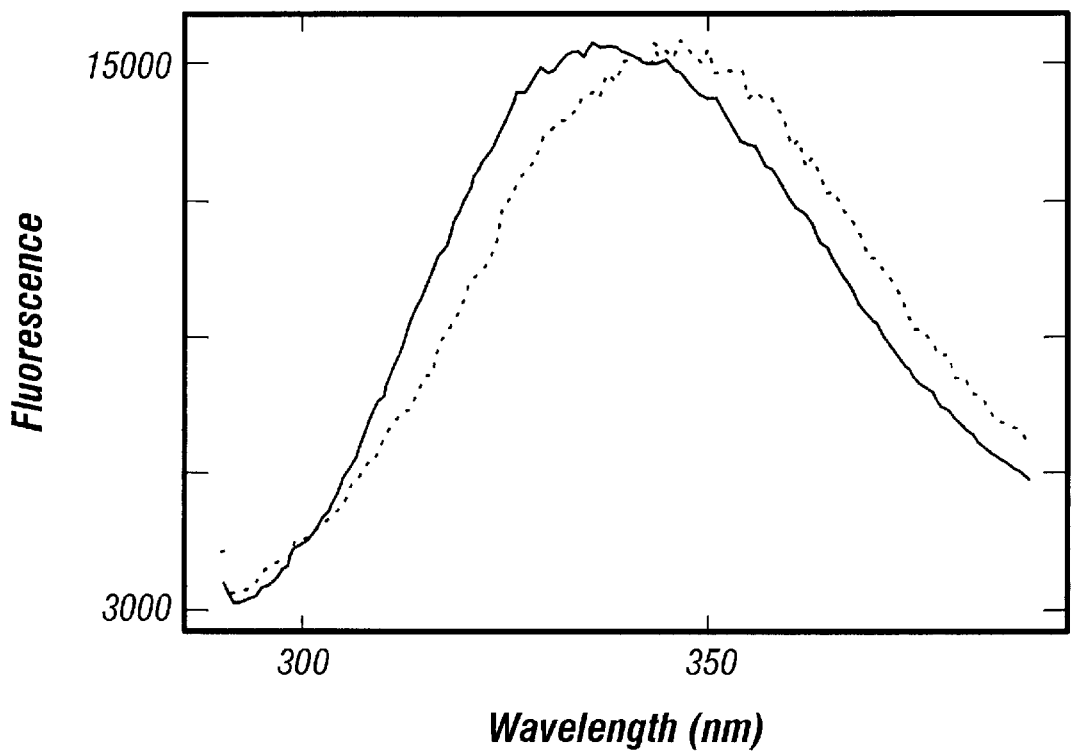
FIG. 8 is the fluorescence spectra of recombinant $K4_2$ in phosphate buffered saline (solid line) and in 4 M GuHCl containing 1 mM DTT (dashed line). Samples (approximately 5 µM) were contained in 1 cm quartz cuvettes and were excited with 280 nm light.

Excitation of $k4_2$ with 280 nm light produced a tryptophan fluorescence with a maximum at 330 nm, indicating partial shielding of tryptophan residues from the solvent. The spectrum is shown in FIG. 8 and is similar to spectra observed for other kringles in their native form (Matsuka, 1990).

Solvent Exposure

Figure 9:
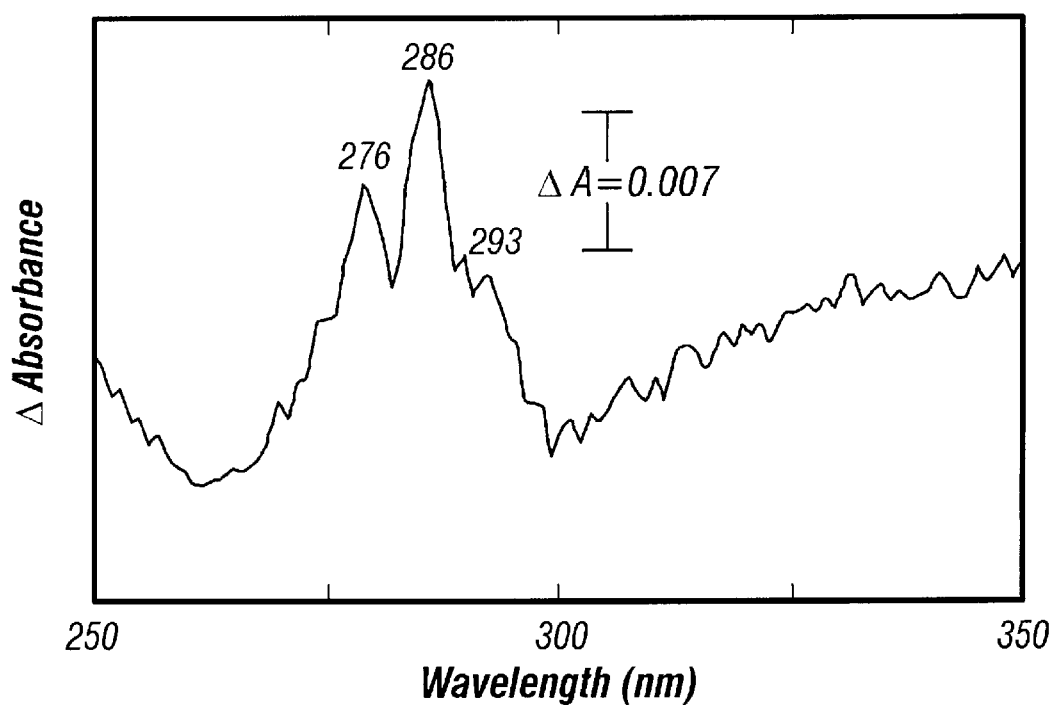
FIG. 9 shows the ultraviolet absorption difference spectrum of $K4_2$ (ca. 10 µM) in 4 M GuHCl containing 1 mM DTT minus $K4_2$ in phosphate buffered saline. The spectral window shown highlights the changes in the electronic transitions of tyrosine and tryptophan residues.

Addition of 4 M GuHCl and 1 mM DTT to the $k4_2$ solution caused a red shift of the fluorescence maximum to ~345 nm, indicating unfolding of the native structure and exposure of buried tryptophan residues to bulk solvent. FIG. 9 illustrates the solvent perturbation difference spectrum induced by treatment of the protein with the denaturants. Buried tyrosine and tryptophan residues are brought into contact with the aqueous solvent as reflected by the differential absorbances at 276 nm (tyrosine), 286 nm (tyrosine and tryptophan) and 293 nm (tryptophan).

Sulfhydryl Group Reactivity $K4_2$ was exposed to a large molar excess of a cysteine specific modifying reagent, 4,4-dithioldipyridine for at least one hour. No reaction was observed in the absorbance at 324 nm monitored during the reaction period. These results indicated that none of the six cysteine residues of $K4_2$ are available for reaction with DTT, etiher because they are involved in disulfide bonding or are buried within the interior of the folded protein.

Reaction of $K4_2$ With Antibodies to Apo (a)

Lipoprotein (a) was injected into mice. Female BALB/C mice were immunized four times in 2–3 week intervals with 50 μg Lp(a) protein which was emulsified with Ribi adjuvant (Ribi Immuno Chem Research, Hamilton, Mont.). Four days after the last boosting, the mice were sacrificed and the immune spleen cells were fused with myeloma cells SP2/0. Two to three weeks later, tissue culture spent media were collected from hybrid growing wells of microtiter plates and tested for Lp(a)-binding monoclonal antibodies. Ascitic fluid was collected from pristane treated female BALB/C mice that were injected with the appropriate hybridoma cells. The fluid was clarified by centrifugation at 3000×g for 10 min and passed over a protein G-Sepharose column. Bound MAb was eluted with 0.1 M glycine, pH 2,5, and immediately titrated to pH 7.4 with 1 M TRIS.

Figure 10:
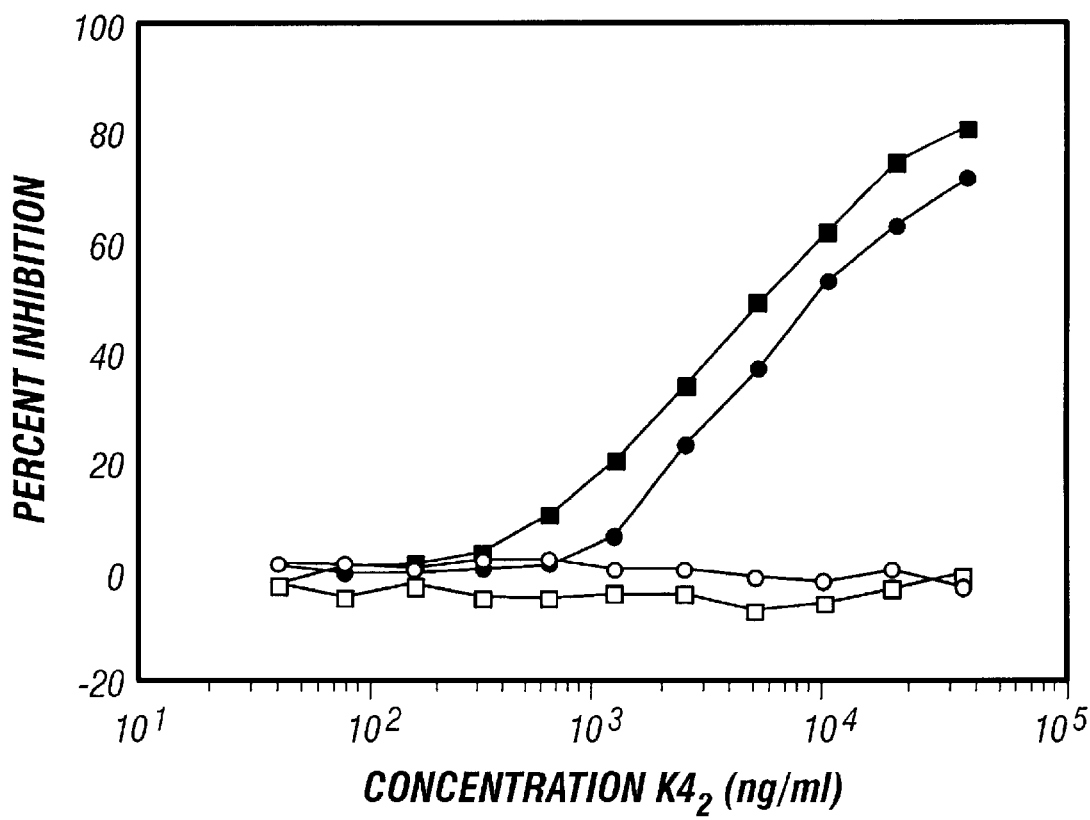
FIG. 10 shows the reactivity of monoclonal antibodies specific to anti apo (a) with "native" and reduced and carboxymethylated $K4_2$ as determined by competitive ELISA. Closed symbols represent "native" $K4_2$ and open symbols represent reduced and carboxymethylated $K4_2$. Values obtained with MAb 4D2 are indicated by circles and those of MAb 1E1 are indicated by squares.

An ELIZA assay was set up in which $K4_2$ competed with lipoprotein (a) for a constant amount of MAb, resulting in identification of two monoclonal antibodies, IEI and 4D2. These MAbs reacted with $K4_2$ purified from whole cell lysate, but not with reduced and carbomethylated $k4_2$, as shown in FIG. 10. This result indicated that K4$_2$ cysteines spontaneously formed disulfide bonds, allowing K4$_2$ to assume its native tertiary structure. The disulfide bonds were also present in the isolated fusion protein, isolated by the method of Example 1 and 2, as indicated by a positive ELISA response which remained unaffected by competition with the reduced and carboxymethylated form of the protein.

PROPHETIC EXAMPLE 7

The availability of pure, recombinant kringle 4 and 5 domains makes possible a specific and convenient assay for blood apo (a). Such an assay will assist in determining serum apo (a) levels which are considered to be positively correlated with a high risk of coronary disease. Although antibodies to apo (a) react with the kringle 4$_2$ domain isolated from apo (a) in accordance with the present invention, monoclonal antibodies to the unique kringle 5 domain are expected to provide increased specificity and sensitivity. The following example illustrates a typical assay, based on ELISA principles, contemplated to be useful in the determination of blood serum apo (a) levels.

Determination of Apo (a) in Serum

Polystyrene microtiter plates will be coated with 100 µl of MAb specific to kringle 4 domains of apo (a)(200–400 ng/well) in 10 mM TRIS, 150 mM NaCl, pH 7.6. The plates will be sealed with a thin adhesive-coated plastic sheet and incubated overnight at room temperature. The next day the unbound antibodies will be removed by washing the plates 3 times, 5 min/wash, with TRIS-saline containing 1% bovine serum albumin. The remaining binding sites in the wells will be blocked for 2 hr with 200 µl of the same wash buffer. After blocking, the plates will be dried, sealed and stored at −20° C. until use.

After equilibrating plates to room temperature, 100 µl of standard Lp(a) or plasma samples (various dilutions) in 0.1 M NaHCO$_3$, 0.5 M NaCl containing 1% BSA and 0.1% Tween-20, pH 8.1, will be added to the wells. The Lp(a) standard may range from 1 ng to 1 µg per well; the plasma samples may be diluted from 1:10 to 1:25,000. The microtiter plates will be incubated 2 h at 32° C. and washed 3 times, 5 min/wash, with NaHCO$_3$ buffer. This will be followed with an incubation for 1 hr at 37° C. with 100 µl of the appropriate dilution of a conjugate of MAb specific to K5 and alkaline phosphatase. After 3 washes, 5 min each, with the bicarbonate buffer, 100 µl of substrate (1 mg/ml p-nitrophenyl phosphate in diethanolamine buffer containing 0.01% HgCl$_2$) will be added to each well. After the appropriate incubation time, the absorbance at 410 nm will be determined.

REFERENCES

The references listed below are incorporated herein by reference to the extent they supplement, explain, provide a background for or teach methodoloby, techniques and/or compositions employed herein.

Castellino, F. J., Ploplis, V. A., Powell, J. R., and Strickland, D. K., "The existence of independent domain structures in human lys77-plasminogen," *J. Biol. Chem.* 256, 4778–4782 (1981).

Cleary, S., Mulkerrin, M. G., and Kelley, R. F., "Purification and characterization of tissue plasminogen activator kringle-2 domain expressed in *Escherichia coli*," *Biochemistry* 28, 1884–1891 (1989).

Copeland, R. A., Ji, H., Halfpenny, A. J., Williams, R. W., Thompson, K. C., Herber, W. K., Thomas, K. A., Bruner, M. W., Ryan, J. A., Marquis-Omer, D., Sanyal, G., Sitrin, R. d., Yamazaki, S., and Middaugh, C. R., "The structure of human acidic fibroblast growth factor and its interaction with heparin," *Arch. Biochem. and Biophys.* 289, 53–61 (1991).

Eaton, D. L., Fless, G. M., Kohr, W. J., McLean, J. W., Xu, Q., Miller, C. G., Lawn, R. M., and Scanu, A. M., "Partial amino acid sequence of apolipoprotein (a) shows that it is homologous to plasminogen," *Proc. Natl. Acad. Sci. USA* 84, 3224–3228 (1987).

Fless, G. M., Rolih, C. A., and Scanu, A. M., "Heterogeneity of human plasma lipoprotein (a): isolation and characterization of the lipoprotein subspecies and their apoproteins," *J. Biol. Chem.* 259, 11470–11478 (1984).

Fless, G. M., ZumMallen, M. E., and Scanu, A. M., "Isolation of apolipoprotein (a) from lipoprotein (a)," *J. Lipid Res.* 26, 1224–1229 (1985).

Fless, G. M., ZumMallen, M. E., and Scanu, A. M., "Physico-chemical properties of apo (a) and Lp(a) derived from the dissociation of human plasma Lp(a)," *J. Biol. Chem.* 261, 8712–8718 (1986).

Gaubatz, J. W., Heideman, C., Gotto, A. M., Morrisett, Jr., J. D., and Dahlen, G. H., "Human plasma lipoprotein (a): Structural properties," *J. Biol. Chem.* 258, 4582–4589 (1983).

Gaubatz, J. W., Ghanem, K. I., Guevara, Jr., J., Nava, M. L., Patsch, W., and Morrisett, J. D., "Polymorphic forms of human apolipoprotein (a): inheritance and relationship of their molecular weights to plasma levels of lipoprotein (a)," *J. Lipid Res.* 31, 603–613 (1990).

Hewick, R. M., Hunkapiller, M. W., Hood, L. E., and Dreyer, W. J., "A gas-liquid solid phase peptide and protein sequenator," *J. Biol. Chem.* 256, 7990–7997 (1981).

Hummel, M., Li, Z., Pfaffinger, D., Neven, L., and Scanu, A. M., "Familial hypercholesterolemia in a rhesus monkey pedigree: Molecular basis of LDL receptor deficiency," *Proc. Natl. Acad. Sci. USA* 87, 3122–3126.

Kratzin, H., Armstrong, V. W., Niehaus, M., Hilschmann, N., and Seidel, N., "Structural relationship of an apolipoprotein (a) phenotype (570 kDa) to plasminogen: homologous kringle domains are linked by carbohydrate-rich regions," *Biol. Chem. Hoppe-Seyler* 368, 1533–1544 (1987).

Kruft, V., Kapp, U., and Wittman-Liebold, B., "On-sequencer pyridylethylation of cysteine residues after protection of amino group by reaction with phenylisothiocyanate," *Anal. Biochem.* 193, 306–309.

Kyte, et al., *J. Mol. Biol.* 157, 105–132 (1982).

Lackner, C., Boerwinkle, E., Leffert, C. C., Rahmig, T., and Hobbs, H., "Molecular basis of apolipoprotein (a) isoform size heterogeneity as revealed by pulsed-field gel electrophoresis," *J. Clin. Invest.* 87, 2153–2161 (1991).

Magnusson, S., Peterson, T. E., Sottrup-Jensen, L., and Clays, H., "Complete primary structure of prothrombin: isolation, structure, and reactivity of ten carboxylated glutamic acid residues and regulation of prothrombin activation by thrombin," in Proteases and Biological Control, Reich, E., Rifkin, D. B., and Shaw, E., eds. (Cold spring Harbor, N.Y.: Cold Spring Harbor Laboratory), 123–149 (1975).

Maina, C. V., Riggs, P. D., Grandea, A. G. III, Slatko, B. E., Moran, L. S., Tagliamonte, J. A., McReynolds, L. A., and Guan, C. di, "An Escherichia coli vector to express and purify foreign proteins by fusion to and separation from maltose-binding protein," *Gene* 74, 365–373.

Matsuka, Y. V., Novokhatny, V. V., and Kudinov, S. A., "Fluorescence spectroscopic analysis of ligand binding to kringle 1+2+3 and kringle 1 fragments from human plasminogen," *Eur. J. Biochem.* 89, 93–97 (1990).

McLean, J. W., Tomlinson, J. E., Kuang, W. J., Eaton, D. L., Chen, E. Y., Fless, G. M., Scanu, A. M., and Lawn, R. M., "cDNA sequence of human apolipoprotein (a) is homologous to plasminogen." *Nature* 330, 132–137 (1987).

Mehnhart, N., Sehl, L. C., Kelley, R. F., and Castellino, F. J., "Construction, expression, and purification of recombinant kringle 1 of human plasminogen and analysis of its interaction with ω-amino acids," *Biochemistry* 30, 1948–1957 (1991).

Morrisett, J. D., Gaubatz, J. W., Knapp, R. D., and Guevara, Jr., J. G., "Structural properties of apo (a): a major apoprotein of human lipoprotein (a)," in Lipoprotein (a), Scanu, A. M. ed. (Academic Press), 53–74 (1990).

Mulichak, A. M., Tulinsky, A., and Ravichandran, K. G., "Crystal and molecular structure of human plasminogen kringle 4 refined at 1.9-A resolution," *Biochemistry* 30, 10576–10588 (1991).

Nagai, K., and Thogersen, H. C., "Generation of β-globin by sequence-specific proteolysis of a hybrid protein produced in *Escherichia coli*," *Nature* 309, 810–812 (1984).

Neu, H. C., and Heppel, L. A., "The release of enzymes from *Escherichia coli* by osmotic shock and during the formation of spheroplasts," *J. Biol. Chem.* 240, 3685–3692 (1965).

Sanger, F., Coulson, A. R., Barrell, B. G., Smith, A. J. H., and Roe, B. A., "Cloning in single-stranded bacteriophage as an aid to rapid DNA sequencing," *J. Mol. Biol.* 143, 161–178 (1980).

Scanu, A. M., and Fless, G. M., "Lipoprotein (a): Heterogeneity and biological relevance," *J. Clin. Invest.* 85, 1709–1715 (1990).

Sherman, D., Kotake, S., Ishibe, N., and Copeland, R. A., "Resolution of the electronic transitions of cytochrome c oxidase: Evidence for two conformational states of ferrous cytochrome a," *Proc. Natl. Acad. USA* 88, 4265–4269 (1991).

Tempst, P., and Riviere, L., "Examination of automated polypeptide sequencing using standard phenyl isothiocyanate reagent and subpicomole high-performance liquid chromatographic analysis," *Anal. Biochem.* 183, 290–300 (1989).

Trexler, M., and Patthy, L., "Folding autonomy of the kringle 4 fragment of human plasminogen," *Proc. Natl. Acad. Sci. USA* 80, 2457–2461.

Trieu, V. N., Zioncheck, T. F., Lawn, R. M., and McConathy, W. J., "Interaction of apolipoprotein (a) with apolipoprotein B-containing lipoproteins," *J. Biol. Chem.* 266, 5480–5485 (1991).

Utermann, G., and Weber, W., "Protein composition of Lp(a) lipoprotein from human plasma," *FEBS* (Fed. Eur. Biochem. Soc.) *Lett.* 154, 357–361 (1983).

Utermann, G., Menzel, H. J., Kraft, H. G., Duba, H. C., Kemmler, H. G., and Seitz, C., "Lp(a) glycoprotein phenotypes-inheritance and relation to Lp(a)-lipoprotein concentration in plasma," *J. Clin. Invest.* 80, 458–465 (1987).

Wilhelm, O. G., Jaskunas, S. R., Vlhaos, C. J., and Bang, N. U., "Functional properties of the recombinant kringle-2 domain of tissue plasminogen activator produced in *Escherichia coli*," *J. Biol. Chem.* 265, 14606–14611 (1990).

Wu, T-P., Padmanabhan K., Tulinsky, A., and Mulichak, A. M., "The refined structure of the ε-aminocaproic acid complex of human plasminogen kringle 4," *Biochemistry* 30, 10589–10594 (1991).

What is claimed is:

1. An isolated and purified Kringle 5 domain of apolipoprotein (a), wherein the Kringle 5 domain is free of Kringle 4 domains of apolipoprotein (a).

2. An isolated and purified Kringle 5 domain of apolipoprotein (a), wherein the Kringle 5 domain is free of other amino acid sequences of apolipoprotein (a).

3. The protein of claim 1, wherein said Kringle 5 domain is linked to β-galactosidase, glutathione-S-transferase, ubiquitin protein or maltose binding protein.

4. A purified protein comprising the Kringle 5 domain of apolipoprotein (a) linked to a fusion protein selected from the group consisting of β-galactosidase, glutathione-S-transferase, ubiquitin protein and maltose binding protein, wherein said protein is prepared by a method comprising the steps of:

(a) obtaining an expression vector comprising:
        (i) a promoter sequence; and
        (ii) a DNA encoding said protein;
    (b) contacting said expression vector with a host cell; and
    (c) purifying the expressed Kringle 5 domain protein.

5. The protein of claim 4, wherein said fusion protein is cleaved to obtain said Kringle 5 domain.

6. A purified Kringle 5 domain of apolipoprotein (a), prepared by a method comprising the steps of:

(a) obtaining an expression vector comprising:
        (i) a promoter sequence; and
        (ii) a DNA encoding a protein comprising a Kringle 5 domain of apolipoprotein (a) linked to a fusion protein selected from the group consisting of β-galactosidase, glutathione-S-transferase, ubiquitin protein and maltose binding protein;
    (b) contacting said expression vector with a host cell;
    (c) purifying the expressed protein; and
    (d) cleaving said fusion protein to obtain said Kringle 5 domain.

7. The protein of claim 6, wherein said Kringle 5 domain is free of Kringle 4 domains of apolipoprotein (a).

8. The protein of claim 6, wherein said Kringle 5 domain is free of other amino acid sequences of apolipoprotein (a).

* * * * *

SEQUENCE LISTING (1) GENERAL INFORMATION:

(iii) NUMBER OF SEQUENCES: 7

(2) INFORMATION FOR SEQ ID NO: 1:

(i) SEQUENCE CHARACTERISTICS:
      (A) LENGTH:     54 base pairs
      (B) TYPE:       nucleic acid
      (C) STRANDEDNESS: single
      (D) TOPOLOGY:   linear (xi) SEQUENCE DESCRIPTION: SEQ ID NO: 1:

GAATTCAGTA AAACCCTCGA TGGATCCTCT AGAGTCGACC TGCAGGCAAG CTTG    54

(2) INFORMATION FOR SEQ ID NO: 2:

(i) SEQUENCE CHARACTERISTICS:
      (A) LENGTH:     30 base pairs
      (B) TYPE:       nucleic acid
      (C) STRANDEDNESS: single
      (D) TOPOLOGY:   linear (xi) SEQUENCE DESCRIPTION: SEQ ID NO: 2:

AGGCCTGAAT TCGCACCGAC TGAGCAGAGG                               30

(2) INFORMATION FOR SEQ ID NO: 3:

(i) SEQUENCE CHARACTERISTICS:
        (A) LENGTH:       33 base pairs
        (B) TYPE:         nucleic acid
        (C) STRANDEDNESS: single
        (D) TOPOLOGY:     linear (xi) SEQUENCE DESCRIPTION: SEQ ID NO: 3:

CTCCGAGGAA GGCTTGTTAC TAGATCTCAG CTG                           33

(2) INFORMATION FOR SEQ ID NO: 4:

(i) SEQUENCE CHARACTERISTICS:
        (A) LENGTH:       130 amino acid residues
        (B) TYPE:         amino acid
        (C) STRANDEDNESS: single
        (D) TOPOLOGY:     linear (xi) SEQUENCE DESCRIPTION: SEQ ID NO: 4:

```
Ser Ser Ser Val Pro Gly Arg Gly Ser Ile Glu Gly Arg Pro Glu Phe
  1               5                  10                  15

Ala Pro Thr Glu Gln Arg Pro Gly Val Gln Glu Cys Tyr His Gly Asn
                 20                  25                  30

Gly Gln Ser Tyr Arg Gly Thr Tyr Ser Thr Thr Val Thr Gly Arg Thr
                 35                  40                  45

Cys Gln Ala Trp Ser Ser Met Thr Pro His Ser His Ser Arg Thr Pro
 50                  55                  60

Glu Tyr Tyr Pro Asn Ala Gly Leu Ile Met Asn Tyr Cys Arg Asn Pro
 65                  70                  75                  80

Asp Ala Val Ala Ala Pro Tyr Cys Tyr Thr Arg Asp Pro Gly Val Arg
                 85                  90                  95

Trp Glu Tyr Cys Asn Leu Thr Gln Cys Ser Asp Ala Glu Gly Thr Ala
                100                 105                 110

Val Ala Pro Pro Thr Val Thr Pro Val Pro Ser Leu Glu Ala Pro Ser
                115                 120                 125

Glu Gln
130
```

(2) INFORMATION FOR SEQ ID NO: 5:

(i) SEQUENCE CHARACTERISTICS:
        (A) LENGTH:       33 base pairs
        (B) TYPE:         nucleic acid
        (C) STRANDEDNESS: single
        (D) TOPOLOGY:     linear (xi) SEQUENCE DESCRIPTION: SEQ ID NO: 5:

GTCGACTCTA GATCATTGTT CGGAAGGAGC CTC                           33

(2) INFORMATION FOR SEQ ID NO: 6:

(i) SEQUENCE CHARACTERISTICS:
        (A) LENGTH:       33 base pairs
        (B) TYPE:         nucleic acid
        (C) STRANDEDNESS: single
        (D) TOPOLOGY:     linear (xi) SEQUENCE DESCRIPTION: SEQ ID NO: 6:

```
ACTACGCCTG AATTCCCTTC TGAACAAGAC TGT                                    33
```

(2) INFORMATION FOR SEQ ID NO: 7:

(i) SEQUENCE CHARACTERISTICS:
        (A) LENGTH:      35 base pairs
        (B) TYPE:        nucleic acid
        (C) STRANDEDNESS: single
        (D) TOPOLOGY:    linear (xi) SEQUENCE DESCRIPTION: SEQ ID NO: 7:

```
GCCAGGCGCT CTAGATTAAT CAAATGAAGA GATGC                                  35
```